(12) United States Patent
Thakur et al.

(10) Patent No.: US 7,267,971 B2
(45) Date of Patent: Sep. 11, 2007

(54) PROCESS FOR PREPARATION OF THERMOSTABLE ENZYME

(75) Inventors: Munna Singh Thakur, Karnataka (IN); Renu Sarath Babu Vegesna, Karnataka (IN); Naikankatte Ganesh Karanth, Karnataka (IN); Mysore Anantharamaiah Kumar, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/395,878

(22) Filed: Mar. 25, 2003

(65) Prior Publication Data

US 2004/0191882 A1    Sep. 30, 2004

(51) Int. Cl.
*C12N 11/14* (2006.01)
*C12N 9/04* (2006.01)
*C12P 19/00* (2006.01)

(52) U.S. Cl. .................. 435/176; 435/190; 435/72
(58) Field of Classification Search ............... 435/190, 435/176, 25, 72; 424/94.4
See application file for complete search history.

(56) References Cited

U.S. PATENT DOCUMENTS 3,519,538 A * 7/1970 Messing et al. ............ 435/176
6,008,319 A * 12/1999 Epstein et al. .............. 530/324
6,124,277 A * 9/2000 Schacht et al. ............. 514/183

OTHER PUBLICATIONS

Environmental Protection Agency's (EPA's) Cameo guide on hazardous chemicals under Section 112(r) of the Clean Air Act, http://www.epa.gov/ ceppo/cameo/help/chapte9h.htm, printed on Nov. 14, 2005.*
Organic Synthesis, Smith, McGraw-Hill, Inc., New York, 1994, pp. 382-384.*
M.D. Gouda et al., "Stability Studies on Immobilized Glucose Oxidase Using an Amperometric Biosensor—Effect of Protein Based Stabilizing Agents", Electroanalysis, vol. 13, No. 10, pp. 849-855 (2001).
M.D. Gouda et al., "Enhancement of Operational Stability of an Enzyme Biosensor for Glucose and Sucrose Using Protein Based Stabilizing Agents", Biosensors and Bioelectronics, vol. 17, pp. 503-507 (2002).

* cited by examiner

*Primary Examiner*—Robert A. Wax
*Assistant Examiner*—Rosanne Kosson
(74) *Attorney, Agent, or Firm*—Greenblum & Bernstein, P.L.C.

(57) ABSTRACT

A process for the preparation of thermostable enzyme glucose oxidase of high Transition temperature ($T_m$) useful for biological processes of high temperature, said process comprising steps of silanizaton of the activated glass beads by evaporative deposition of Aminopropyl triethoxysilane in acetone, heating the silanated glass beads overnight at about 115° C., treating the heated glass beads with glutaraldehyde in phosphate buffer of pH about 6.0 for one hour each, both with and without vacuum, exposing the treated beads to the enzyme at about 30° C. and for time duration ranging between 3-5 hours with intermittent shaking, reducing the Schiff's base obtained in preceeding step by treating the beads of step (d) with sodium cyanoborohydride, obtaining thermostable enzyme immobilized on the beads, blocking the unoccupied regions of the glass beads with glycine, and a method of using the said thermostable enzymes, and a thermostable enzyme thereof.

16 Claims, No Drawings

PROCESS FOR PREPARATION OF THERMOSTABLE ENZYME

FIELD OF THE PRESENT INVENTION

A process for the preparation of thermostable enzyme glucose oxidase of high Transition temperature ($T_m$) useful for biological processes of high temperature, said process comprising steps of silanizaton of the activated glass beads by evaporative deposition of Aminopropyl triethoxysilane in acetone, heating the silanated glass beads overnight at about 115° C., treating the heated glass beads with glutaraldehyde in phosphate buffer of pH about 6.0 for one hour each, both with and without vacuum, exposing the treated beads to the enzyme at about 30° C. and for time duration ranging between 3-5 hours with intermittent shaking, reducing the Schiff's base obtained in preeceding step by treating the beads of step (d) with sodium cyanoborohydride, obtaining thermostable enzyme immobilized on the beads, blocking the unoccupied regions of the glass beads with glycine, and a method of using the thermostable enzymes, and a thermostable enzyme thereof.

BACKGROUND AND PRIOR ART OF THE INVENTION

Reference may be made here to Gouda, M. D., Thakur, M. S. and Karanth, N. G, (2001), "Stability Studies on Immobilized Glucose Oxidase Using an Amperometric Biosensor-Effect of Protein Based Stabilizing Agents", *Electroanalalysis* 13 (10) 849-855, wherein they have reported on the stabilization of glucose oxidase against thermal denaturation by the use of protein based stabilizing agents. The protein based stabilizing agents are expensive and are suitable for immobilization of enzymes on Membranes and are not suitable for use in Flow Injection Analysis based systems where column reactors are usually used with enzymes immobilized on solid matrices. Therefore present invention will be useful in immobilization of enzymes in a simpler manner to be used in Flow Injection Analysis based biosensor system or any other bioreactor for bioconversions with increased stability.

Reference may be made to Boahong, L., Renqi Hu and Jiaqi, D., (1997), "Characterization of immobilization of an enzyme in a modified Y-Zeolite matrix and its application to an amperometric glucose biosensor"., *Anal. Chem.*, 69, 2343-2348, wherein they have reported the stabilization of glucose oxidase by immobilization of the enzyme in a modified Y-Zeolite matrix for its application to an amperometric glucose biosensor using carbon paste electrodes. The draw back is that it is not suitable for Flow Injection Analysis systems as Y-Zeolite matrix is in the form of a fine powder and will hinder the flow of liquids in a packed bed column.

Silanization as a technique has been used for the surface modification of solid supports for the efficient immobilization of enzymes, wherein the non-reactive groups in silane such as alkyls provide hydrophobicity (Slobodianokova, 1979) and render the surface charged. The efficiency of this action is dependent on the surface roughness, concentration and type of used (Bhatia. 1999, Crass 1999) the concentration of silane used for this purpose is generally lower than 2%. However, there are no reports on the use of silane for increasing stability of immobilized enzymes.

OBJECTS OF THE PRESENT INVENTION

The main objective of the present invention is to develop a process for the preparation of thermostable enzymes.

Another main object of the present invention is to develop a process for the preparation of thermostable enzyme glucose oxidase.

Yet another object of the present invention is to develop a method of using thermostable enzyme at high temperature.

SUMMARY OF THE PRESENT INVENTION

A process for the preparation of thermostable enzymes of high Transition temperature ($T_m$) useful for biological processes of high temperature, said process comprising steps of silanizaton of the activated glass beads by evaporative deposition of Aminopropyl triethoxysilane in acetone, heating the silanated glass beads overnight at about 115° C., treating the heated glass beads with glutaraldehyde in phosphate buffer of pH about 6.0 for one hour each, both with and without vacuum, exposing the treated beads to the enzyme at about 30° C. and for time duration ranging between 3-5 hours with intermittent shaking, reducing the Schiff's base obtained in preeceding step by treating the beads of step (d) with sodium cyanoborohydride, obtaining thermostable enzyme immobilized on the beads, blocking the unoccupied regions of the glass beads with glycine, and a method of using the thermostable enzyme glucose oxidase, and a thermostable enzyme thereof.

DETAILED OF THE PRESENT INVENTION

Accordingly, the present invention relates to a process for the preparation of thermostable enzymes of high Transition temperature ($T_m$) useful for biological processes of high temperature, said process comprising steps of silanizaton of the activated glass beads by evaporative deposition of Aminopropyl triethoxysilane in acetone, heating the silanated glass beads overnight at about 115° C., treating the heated glass beads with glutaraldehyde in phosphate buffer of pH about 6.0 for one hour each, both with and without vacuum, exposing the treated beads to the enzyme at about 30° C. and for time duration ranging between 3-5 hours with intermittent shaking, reducing the Schiff's base obtained in preeceding step by treating the beads of step (d) with sodium cyanoborohydride, obtaining thermostable enzyme immobilized on the beads, blocking the unoccupied regions of the glass beads with glycine, and a method of using the thermostable enzymes, and a thermostable enzyme thereof.

A process for the preparation of thermostable enzyme glucose oxidase of high Transition temperature ($T_m$) useful for biological processes of high temperature, said process comprising steps of:

silanizaton of the activated glass beads by evaporative deposition of Aminopropyl triethoxysilane in acetone, heating the silanated glass beads overnight at about 115° C., treating the heated glass beads with glutaraldehyde in phosphate buffer of pH about 6.0 for one hour each, both with and without vacuum, exposing the treated beads to the enzyme at about 30° C. and for time duration ranging between 3-5 hours with intermittent shaking, reducing the Schiff's base obtained in preeceding step by treating the beads of step (d) with sodium cyanoborohydride, obtaining thermostable enzyme immobilized on the beads, blocking the unoccupied regions of the glass beads with glycine.

In still another embodiment of the present invention, wherein the glass beads are of diameter ranging between 0.5-0.75 mm.

In still another embodiment of the present invention, wherein the concentration of Aminopropyl triethoxysilane is ranging between 1-8%.

In still another embodiment of the present invention, wherein the processed enzyme is stable at temperature as high as 80° C. for time duration of 1-4 hours.

In still another embodiment of the present invention, wherein the concentration of glutaraldehyde is ranging between 2.0-3.0%.

In still another embodiment of the present invention, wherein the concentration of glutaraldehyde is about 2.5%.

In still another embodiment of the present invention, wherein the concentration of phosphate buffer is ranging between 100-300 mM.

In still another embodiment of the present invention, wherein treating the beads with sodium cyanoborohydride for time duration of 1-3 hours at about 300C, and subsequently, for about 12-24 hours at about 4° C., In still another embodiment of the present invention, wherein the concentration of sodium cyanoborohydride is ranging between 25-75 mg/gram of glass beads.

In still another embodiment of the present invention, wherein the concentration of glycine is ranging between 0.05-0.5M.

In still another embodiment of the present invention, wherein the enzyme is glucose oxidase.

In still another embodiment of the present invention, wherein activating the beads by boiling them in about 5% nitric acid at about 80° C. for about 3 hours.

In still another embodiment of the present invention, wherein exposing enzyme of International units ranging between 500-1500 to one gram of beads.

In still another embodiment of the present invention, wherein the immobilized enzyme is stored at 4° C. in buffer containing sodium azide of concentration ranging between 0.001-005%.

In still another embodiment of the present invention, wherein the thermostable enzyme shows transition temperature $T_m$ of about 80° C.

In still another embodiment of the present invention, wherein a method of using the thermostable enzyme glucose oxidase in enzymatic processes at temperature as high as about 80° C., said method comprising steps of exposing the enzyme to the substrate, and obtaining desired product.

In still another embodiment of the present invention, wherein the said enzymes are used bioreactors.

In still another embodiment of the present invention, wherein the said enzymes are used in Flow Injection Analysis based biosensors.

In still another embodiment of the present invention, wherein the enzymatic processes are food and fermentation processes.

In still another embodiment of the present invention, the enzyme in the method is Glucose oxidase.

In still another embodiment of the present invention, wherein useful in enzymatic process of temperature as high as about 80° C.

In still another embodiment of the present invention, wherein enzyme as stated above is Glucose oxidase.

The present invention is related to a Process for preparation of thermostable enzyme useful for bioreactor applications, particularly for applications in Flow Injection Analysis based Biosensors.

In still another embodiment of the present invention, wherein thermal stability of enzymes is important for use in immobilized enzyme based biosensors, which have applications in monitoring food and fermentation processes. Glucose oxidase is the enzyme used in the glucose biosensor and increasing its thermal stability is relevant to its practical applications. Thermal stability of the enzymes is also required in biochemical processes, which require higher temperatures. Most of the enzymes and biological derived materials are heat labile and cannot be used above 50-60° C. Some of the enzymes can be stabilized by using immobilization techniques by incorporating some stabilizers. The stabilized enzyme bioreactor can be used in applications at higher temperatures, such as protein immobilization studies and preparation of heat stable probes in biosensors for monitoring of processes and for enzymatic bioconversions.

In still another embodiment of the present invention, wherein In an embodiment of the present invention the silanization of glass beads is done by evaporative deposition of 1-8% γ-aminopropyl triethoxysilane.

In still another embodiment of the present invention, wherein In another embodiment of the present invention the sodium cyanoborohydride used for reducing the Schiff's bases formed during coupling of the enzyme to the activated support was at a level of 25-75 mg per gram of glass beads.

In yet another embodiment of the present invention, the concentration of glycine used for blocking the free sites on the immobilized enzyme support was in the range 0.05-0.15M.

Cleaning the glass beads (0.5-0.75 mm dia) was done by rinsing with distilled water, boiling in concentrated nitric acid for 1 hour, activation by boiling the beads in 5% nitric acid at 80° C. for 3 hours and subsequent washing with distilled water 3-4 times and silanization by evaporative deposition of aminopropyl triethoxysilane in acetone. Evaporative deposition of aminopropyl triethoxysilane was done by the reported procedure (Weetal, H., (1976), Covalent coupling methods for inorganic support materials, in: K. Moshbach (Ed.), *Methods in Enzymology*, Vol. 44, Academic Press, New York, Ch. 10, pp. 134-148), in which a solution of silane in 25 ml of dry acetone was prepared.

In still another embodiment of the present invention, wherein One gram of the activated glass beads were added to the silane in a flask and the reaction carried out for 3 hours at room temperature. Acetone was then evaporated by application of vacuum for the deposition of silane over the glass bead surface. The beads were then incubated overnight at 115° C. in an oven, treatment with 2.5% glutaraldehyde in phosphate buffer for one hour each with and without vacuum and a thorough wash for 3-4 times each with distilled water and buffer; 1000 international units of glucose oxidase dissolved in buffer is mixed with one gram of the silanized beads and kept at room temperature for 3 hours with intermittent shaking; 25-75 mg of sodium cyanoborohydride was then added to reduce the Schiff's bases formed, kept for 1-3 hrs at room temperature and then 12-24 hrs at 4° C.

In still another embodiment of the present invention, wherein The free sites on the immobilized enzyme support were blocked by adding 0.05-0.15 M Glycine solution, keeping at room temperature for one hour and then washing thrice with distilled water and buffer. 0.002% sodium azide was added to the buffer to prevent microbial contamination and the immobilized enzyme was stored at 4° C.

In still another embodiment of the present invention, wherein Thermal stability studies on soluble glucose oxidase are carried out by dissolving 100 international units of glucose oxidase in 1 ml of 100 mM phosphate buffer at pH 6.0 and incubating the enzyme solution in a water bath at temperatures of 30-75° C. in steps of 5° C. for a period of 3 hours. Samples are drawn at every 30 minutes and the enzyme activity is checked by incubating the enzyme with 50-g/l solution of glucose and the activity is recorded as a drop in the dissolved oxygen content sensed by an amperometric electrode.

In still another embodiment of the present invention, wherein Thermal stability studies on glucose oxidase immobilized on glass beads using different concentrations of silane are conducted by suspending the immobilized enzyme preparation in 100 mM phosphate buffer at pH 6.0 and incubation in a water bath at temperatures of 30-75° C. in steps of 5° C. for a period of 3 hours. Samples are drawn every 30 minutes and the residual activity is determined by loading the immobilized enzyme sample into a polycarbonate column of 3.5 mm internal diameter and 40 mm length, taking care to avoid entrapment of air bubbles in the column and fixing it into a Flow Injection Analysis System described below.

In still another embodiment of the present invention, wherein The Flow Injection Analysis system consists of two pumps for the buffer and sample respectively. The sample is injected through a valve, which can be controlled either manually or automatically. The sample is then dialyzed against the buffer, which flows at a rate of 0.8-ml/minute. The dialyzed sample then passes through the immobilized enzyme column where the biochemical reaction takes place, causing a drop in the dissolved oxygen, which in turn is sensed by the dissolved oxygen electrode in terms of drop in voltage.

In still another embodiment of the present invention, wherein Freshly prepared glucose solution in phosphate buffer of pH 6.5 molarity of 50 mM with 0.002% sodium azide used to prevent microbial contamination is kept for four hours for mutarotation and is injected at the rate of 200 µl/minute for 30 seconds. The enzyme activity results in a continuous drop in the electrode output voltage, to reach a minimum in about 2 minutes time before rising. The difference between the base line and the minimum value in the voltage response is plotted against glucose concentration. The operation of the Flow Injection Analysis system is as described in literature (Kumar, M. A., Thakur, M. S., Senthuran, S., Senthuran, V., Karanth, N. G. Hatti-Kaul, R. and Mattiasson, B., 2001).

In still another embodiment of the present invention, wherein 50-g/l solution of glucose is passed through the immobilized enzyme column and the glucose oxidase activity is measured as a drop in the dissolved oxygen content sensed by an amperometric electrode.

In still another embodiment of the present invention, wherein the residual activity was calculated by the formula:

% Residual activity $(A) = [b/a] \times 100$

Where, a=activity before heat treatment and b=activity after heat treatment.

For all the enzyme stability experiments the glucose concentration in the sample used is 50 g/l and the effect of temperature in the range of 25-75° C. on the stability of glucose oxidase with different concentrations of aminopropyl triethoxysilane is studied.

Transition temperature $(T_m)$ is the maximum temperature at which the enzyme retains 50% of its initial activity after 3 hours incubation.

Half-life of the enzyme (T½) is the time at which the enzyme retains 50% of its initial activity and was determined at 70° C. temperature.

In still another embodiment of the present invention, wherein The novelty of the present invention is the stabilization of the immobilized enzymes without modifying the enzyme or use of any additives except for modification of the support for immobilization.

The following examples are given by way of illustration of the present invention only and therefore should not be construed to limit the scope of the invention.

EXAMPLE 1

One gram of Glass beads of 0.5-0.75 mm diameter are first cleaned with distilled water, then boiled in concentrated nitric acid for 1 hour and activated by boiling in 5% nitric acid at 80° C. for 3 hours and subsequent washing with distilled water 4 times. Silanization of the glass beads is done by evaporative deposition of 2% silane in acetone (Weetal, 1969). The silanized supports are heated at 115° C. overnight in an oven and then treated with 2.5% glutaraldehyde in phosphate buffer for one hour each with and without vacuum. The supports are then thoroughly washed three times each with distilled water and buffer.

1000 international units of glucose oxidase enzyme dissolved in buffer is mixed with one gram of the support and kept at a temperature of 30° C. for 3 hours with intermittent shaking. 50 mg of Sodium cyanoborohydride is then added to the above solution to reduce the schiff's bases formed, kept for one hour at a temperature of 30° C. and then for 19 hours at 4° C. The immobilized enzyme support is washed with water and buffer five times each. Blocking the unoccupied regions of the support is done by adding 0.1 M Glycine solution, keeping at a temperature of 30° C. for one hour and then washing thrice each with distilled water and buffer. 0.002% sodium azide is added to the buffer to prevent microbial contamination. The immobilized enzyme preparation is tested for thermal stability as described earlier and showed a transition temperature $T_m$ of 65° C. and a half-life $T_{1/2}$=1½ hours. The activity retained after 3 hours is 92% of the initial value.

EXAMPLE 2

The immobilization of glucose oxidase enzyme is carried out as in example 1, except that a silane concentration of 4% is used. The activity retained after 3 hours is 250% of the initial value and the transition temperature increased to 75° C. with a half life (T ½) of 19 hours.

EXAMPLE 3

The immobilization of glucose oxidase enzyme is carried out as in example 2, except that a silane concentration of 6% is used. The activity retained after 3 hours is 60% of the initial value and the transition temperature is 70° C. with a T ½ of 13 hrs.

EXAMPLE 4

100 international units of the free glucose oxidase enzyme is dissolved in 1 ml of 100-mM phosphate buffer at pH 6.0 and tested for thermal stability. The activity retained after 3 hours is 5.2% of the initial value and the transition temperature $T_m$ of the soluble enzyme is 45.6° C. with a half-life $T_{1/2}=\frac{1}{2}$ hour.

The main advantages of the present invention are:
1. The stabilized enzyme system can be used in applications at higher temperatures, such as protein immobilization studies and also in biosensors for monitoring of processes.
2. This system can be used in the preparation of heat stable probes for biosensor applications.
3. Glass beads are an economical support for immobilization of enzymes and will be suitable for application in packed bed reactors and columns for use in Flow Injection Analysis system for on-line measurement of analytes.
4. Heat labile enzymes or biological materials can be stabilized using appropriate concentration of silane and can be used at higher temperature. This method of stabilization using silanization has the potential to be used for other silicate-containing materials as immobilization matrix.

The invention claimed is:

1. A process for preparing thermostable glucose oxidase of transition temperature ($T_m$) of about 80° C. that is useful for biological processes of high temperature, said process comprising:
   a. silanization of activated glass beads by evaporative deposition of aminopropyl triethoxysilane in acetone, at a concentration of aminopropyl triethoxysilane ranging between 1-8%, forming silanated glass beads;
   b. heating the silanated glass beads overnight at about 115° C. to obtain heated glass beads;
   c. treating the heated glass beads with glutaraldehyde in a phosphate buffer of pH about 6.0 for one hour with and one hour without vacuum to obtain treated beads;
   d. exposing the treated beads to glucose oxidase at about 30° C. and for a time duration ranging between 3-5 hours with intermittent shaking obtaining Schiff's base;
   e. reducing the Schiff's base obtained in (d) by treating the beads with sodium cyanoborohydride;
   f. obtaining thermostable glucose oxidase immobilized on the beads having a transition temperature ($T_m$) of about 80° C.; and
   g. blocking unoccupied regions of the glass beads with glycine.

2. A process as claimed in claim 1, wherein the glass beads are of a diameter ranging between 0.5-0.75 mm.

3. A process as claimed in claim 1, wherein the concentration of aminopropyl triethoxysilane ranges between 2-6%.

4. A process as claimed in claim 1, wherein the processed thermostable glucose oxidase is stable at temperature as high as 80° C. for a time duration of 1-4 hours.

5. A process as claimed in claim 1, wherein the glutaraldehyde has a concentration ranging between 2.0-3.0%.

6. A process as claimed in claim 5, wherein the glutaraldehyde has a concentration of about 2.5%.

7. A process as claimed in claim 1, wherein the phosphate buffer has a concentration ranging between 100-300 mM.

8. A process as claimed in claim 1, wherein treating the beads with sodium cyanoborohydride comprises treating the beads for a time duration of 1-3 hours at about 300° C., and subsequently, for a time duration of about 12-24 hours at about 4° C.

9. A process as claimed in claim 1, wherein the sodium cyanoborohydride has a concentration ranging between 25-75 mg/gram of glass beads.

10. A process as claimed in claim 1, wherein the glycine has a concentration ranging between 0.05-0.5M.

11. A process as claimed in claim 1, further comprising activating the glass beads by boiling them in about 5% nitric acid at about 80° C. for about 3 hours.

12. A process as claimed in claim 1, wherein exposing the treated beads to glucose oxidase comprises exposing one gram of beads to 500-1500 International Units of glucose oxidase.

13. A process as claimed in claim 1, wherein the immobilized glucose oxidase is stored at 4° C. in buffer containing sodium azide of a concentration ranging between 0.001-0.005%.

14. A process for preparing thermostable glucose oxidase of transition temperature ($T_m$) of 65° C. that is useful for biological processes of high temperature, said process comprising:
   a. silanization of activated glass beads by evaporative deposition of aminopropyl triethoxysilane in acetone, at a concentration of aminopropyl triethoxysilane ranging between 1-8%, forming silanated glass beads;
   b. heating the silanated glass beads overnight at about 115° C. to obtain heated glass beads;
   c. treating the heated glass beads with glutaraldehyde in a phosphate buffer of pH about 6.0 for one hour with and one hour without vacuum to obtain treated beads:
   d. exposing the treated beads to glucose oxidase at about 30° C. and for a time duration ranging between 3-5 hours with intermittent shaking obtaining Schiff's base;
   e. reducing the Schiff's base obtained in (d) by treating the beads with sodium cyanoborohydride;
   f. obtaining thermostable glucose oxidase immobilized on the beads having a transition temperature ($T_m$) of 65° C.; and
   g. blocking unoccupied regions of the glass beads with glycine.

15. A process for preparing thermostable glucose oxidase of transition temperature ($T_m$) of 70° C. that is useful for biological processes of high temperature, said process comprising:
   a. silanization of activated glass beads by evaporative deposition of aminopropyl triethoxysilane in acetone, at a concentration of aminopropyl triethoxysilane ranging between 1-8%, forming silanated glass beads:
   b. heating the silanated glass beads overnight at about 115° C. to obtain heated glass beads;
   c. treating the heated glass beads with glutaraldehyde in a phosphate buffer of pH about 6.0 for one hour with and one hour without vacuum to obtain treated beads:
   d. exposing the treated beads to glucose oxidase at about 30° C. and for a time duration ranging between 3-5 hours with intermittent shaking obtaining Schiff's base:
   e. reducing the Schiff's base obtained in (d) by treating the beads with sodium cyanoborohydride:
   f. obtaining thermostable glucose oxidase immobilized on the beads having a transition temperature ($T_m$) of 70° C.; and
   g. blocking unoccupied regions of the glass beads with glycine.

16. A process for preparing thermostable glucose oxidase of transition temperature ($T_m$) of 75° C. that is useful for biological processes of high temperature, said process comprising:
   a. silanization of activated glass beads by evaporative deposition of aminopropyl triethoxysilane in acetone, at a concentration of aminopropyl triethoxysilane ranging between 1-8%, forming silanated glass beads;

b. heating the silanated glass beads overnight at about 115° C. to obtain heated glass beads;
c. treating the heated glass beads with glutaraldehyde in a phosphate buffer of pH about 6.0 for one hour with and one hour without vacuum to obtain treated beads;
d. exposing the treated beads to glucose oxidase at about 30° C. and for a time duration ranging between 3-5 hours with intermittent shaking obtaining Schiff's base;
e. reducing the Schiff's base obtained in (d) by treating the beads with sodium cyanoborohydride;
f. obtaining thermostable glucose oxidase immobilized on the beads having a transition temperature ($T_m$) of 75° C.; and
g. blocking unoccupied regions of the glass beads with glycine.

* * * * *